United States Patent [19]

Nieuwstad

[11] Patent Number: 5,009,227

[45] Date of Patent: Apr. 23, 1991

[54] ENDOTRACHEAL TUBE HOLDER

[76] Inventor: Peter P. Nieuwstad, 12374 NE. 116th La., Kirkland, Wash. 98034

[21] Appl. No.: 410,429

[22] Filed: Sep. 21, 1989

[51] Int. Cl.⁵ .............................................. A61M 16/00
[52] U.S. Cl. ........................... 128/207.17; 128/200.26; 128/207.14; 128/DIG. 26
[58] Field of Search .................... 128/200.26, 207.14, 128/207.15, 207.17, DIG. 26

[56] References Cited

U.S. PATENT DOCUMENTS

| | | | |
|---|---|---|---|
| 4,167,946 | 9/1979 | Sandstrom | 128/207.17 |
| 4,246,897 | 1/1981 | Muto | 128/207.15 |
| 4,249,529 | 2/1981 | Nestor et al. | 128/DIG. 26 |
| 4,256,099 | 3/1981 | Dryden | 128/207.15 |
| 4,270,529 | 6/1981 | Muto | 128/200.26 |
| 4,313,437 | 2/1982 | Martin | 128/207.17 |
| 4,425,911 | 1/1984 | Luomanen et al. | 128/200.26 |
| 4,449,527 | 5/1984 | Hinton | 128/207.17 |
| 4,744,358 | 5/1988 | McGinnis | 128/207.17 |
| 4,896,667 | 1/1990 | Magnusen et al. | 128/207.14 |
| 4,906,234 | 3/1990 | Voychehovski | 128/207.17 |

Primary Examiner—Edgar S. Burr
Assistant Examiner—Aaron J. Lewis
Attorney, Agent, or Firm—Richard C. Litman

[57] ABSTRACT

An endotracheal tube holder is provided which has the capability to hold both an endotracheal tube and a feeding tube in a side by side relationship. Two separate passageways are provided to hold each tube. A surrounding collet provides compression force to hold the endotracheal tube in position relative to the holder. The holder is provided with attachments for a headband that is affixed to flexible wings on either side of the holder. A model for premature or newborn infants is provided with a removable soft sleeve that fits over the mouth portion of the holder so that the gums are not inflamed by friction with the hard surface of the holder which serves as a bite block.

9 Claims, 2 Drawing Sheets

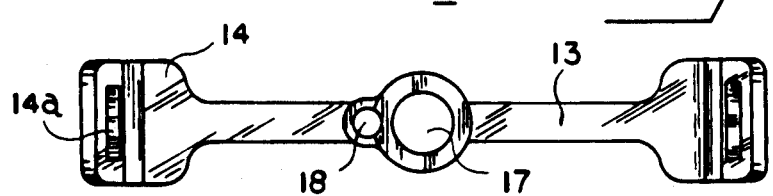
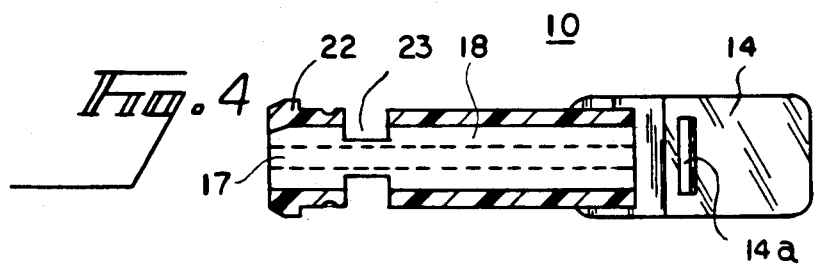
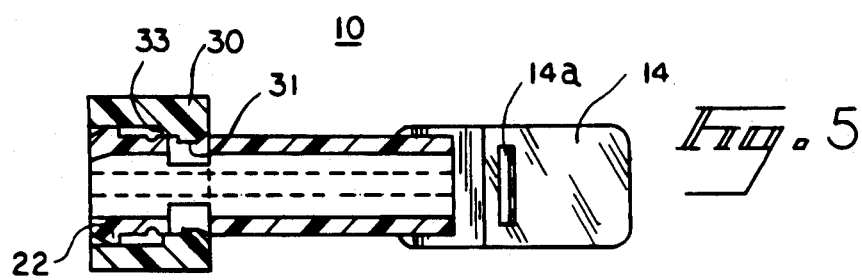
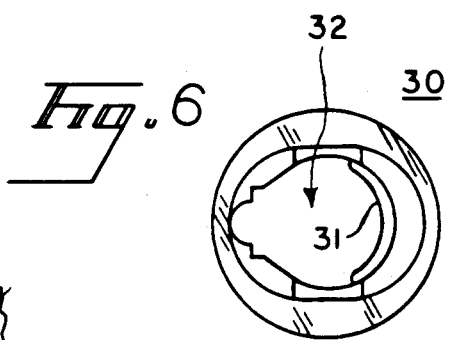
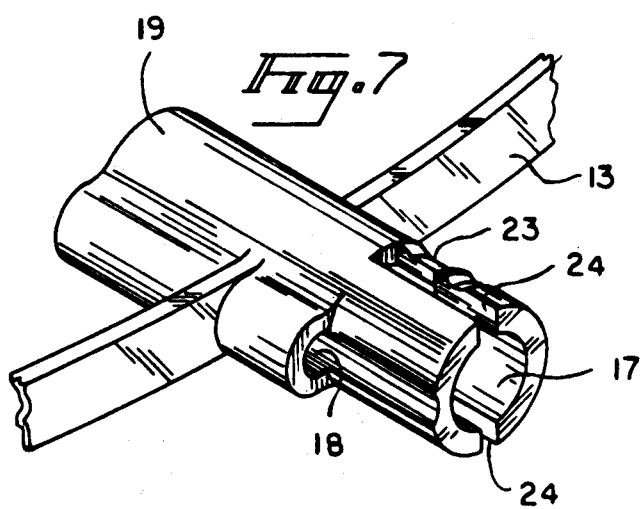

ENDOTRACHEAL TUBE HOLDER

BACKGROUND OF THE INVENTION

1. Field of the Invention

The present invention relates to devices used to hold medical tubes onto a patient. The present invention in particular relates to endotracheal tube holders that are mounted around the patient's head and over the mouth, and can also hold a feeding tube adjacent the endotracheal tube.

The present invention also addresses the problem of clearing the patient's throat of mucous secretions that collect in the rear of the mouth region. The patient usually is not able to swallow due to the tubes in the throat and needs to have these secretions removed by mechanical or outside means. The present invention provides means to insert a secondary tube into the patient's mouth in order to periodically remove these secretions before they choke the patient.

Feeding tubes are usually inserted through the nasal passages of a patient. These feeding tubes leave mucosal scarring and associated bleeding. The present invention allows for the feeding tubes to be inserted down the throat of the patient and not the sensitive nasal passages. This serves to minimize any discomfort and damage to the patient.

2. Description of the Prior Art

The following is a discussion of patents which are felt to relate to the present invention, but in no way disclose, either singly or in combination, the present invention.

U.S. Pat. No. 3,946,742 issued to Eross discloses a tube retainer which extends into the mouth and which is preferably formed of hardened plastic material to resist deformation and collapse when clamped between the patient's teeth.

U.S. Pat. No. 4,223,671 issued to Muto also discloses a tubular portion which extends into the patient's mouth and serves as a bite block.

U.S. Pat. No. 4,683,882 issued to Laird discloses an endotracheal tube holder for use on a child.

Notice that none of the above prior art has provision for holding both an endotracheal tube and a feeding tube adjacent one another simultaneously. Prior to this present invention, feeding tubes were inserted separately into a patient's nasal passages and down through the esophagus to the stomach. This was done to keep the feeding tube from being entangled with the endotracheal . tube. The applicant's present device keeps these two tubes separated so that they will not become entangled. They can then both be inserted into the patient's mouth thereby relieving the discomfort to the patient of having feeding tubes inserted down the nasal passages. The present invention also allows for access into the patient's mouth with the endotracheal tube in place in order to perform any additional functions that are necessary.

SUMMARY OF THE INVENTION

The present invention comprises a medical tube holder having two curved pliant wings extending out from either side from a central tubular member. The wings are pliable so that they can conform to the outline of the face of the wearer. The central tubular member has two distinct passageways through it. A large central passageway is for holding the endotracheal tube. A cantilevered snap lock collet holds it in place by compressing the tubular member. An offset smaller passageway is used for holding a feeding tube. Thus the present device can keep two different tubes in position at once.

The pliant wings have VELCRO attached to both their inside and outside surfaces so that a headband having a reciprocal mating surface may be used to secure the endotrachial tube holder the wearer's head. Cheekpads would be mounted onto the inside VELCRO areas. The VELCRO allows for quick and easY size adjustment and replacement of the headband or cheekpads when they become soiled with blood or secretions. The foam is soft and non-elastic. A non-elastic headband is important with neonates because an elastic headband would prevent the necessary free expansion and contraction of the cranial bones. The cheekpads allow for the device to contour against the outline of a patient's face. They also serve as a comfort device when the patient's cheeks rest on them.

The tubular member is elongated so that it extends into the wearer's mouth. The tubular member has a hardened section that acts as a bite block, preventing the sometimes convulsive patient from biting down on and sealing off the endotrachial and feeding tubes. Over this hard bite block goes a sleeve of soft rubbery that would slip over the central tube holder and act as a pacifier and as a soft cushion for a baby's or elderly person's naked gums. More importantly though it serves to help reduce the condition known as cleft palate. This condition results from prolonged pressure on the palate of the upper mouth by an endotracheal tube. The rubber sleeve serves to spread out the area of contact between the tube and the palate. This will save the patient from any additional corrective surgery that has to be done after the prolonged usage of an endotracheal tube. The soft sleeve also serves to prevent any fracturing of the bite block and any internal damage that the fractural elements would cause to a patient.

Accordingly, it is one object of the present invention to provide an medical tube holder that can hold in position on a wearer two different tubes at once.

It is another object of the present invention to provide an endotracheal tube holder having a VELCRO attachment means for quick and easy headband adjustment.

It is yet another object of the present invention to provide an endotracheal tube holder having a VELCRO attachment means for securing cheekpads in order to cushion the side of a patient's face.

It is a further object of this present invention to provide an endotracheal tube holder with a hardened central tubular member that extends into the mouth of the user to act as a bite block.

It is yet another object of the present invention to provide an endotracheal tube holder with a soft sleeve over the central tubular member to act as a cushion for a wearer having naked gums and as a means to prevent cleft palate.

These and other objects of the present invention will become readily apparent upon further review of the attached specification and drawings.

BRIEF DESCRIPTION OF THE DRAWINGS

FIG. 3 shows a top view of the endotracheal tube holder.

FIG. 4 shows a cross-sectional view of the endotracheal tube holder.

FIG. 5 shows a cross-sectional view of the endotracheal tube holder and attached collet.

FIG. 6 shows a top plan view of the collet.

FIG. 7 shows a perspective view of the endotracheal tube holder detailing the tubular member.

Like reference characters denote similar features consistently throughout the drawings.

DESCRIPTION OF THE PREFERRED EMBODIMENT

Figure 1:
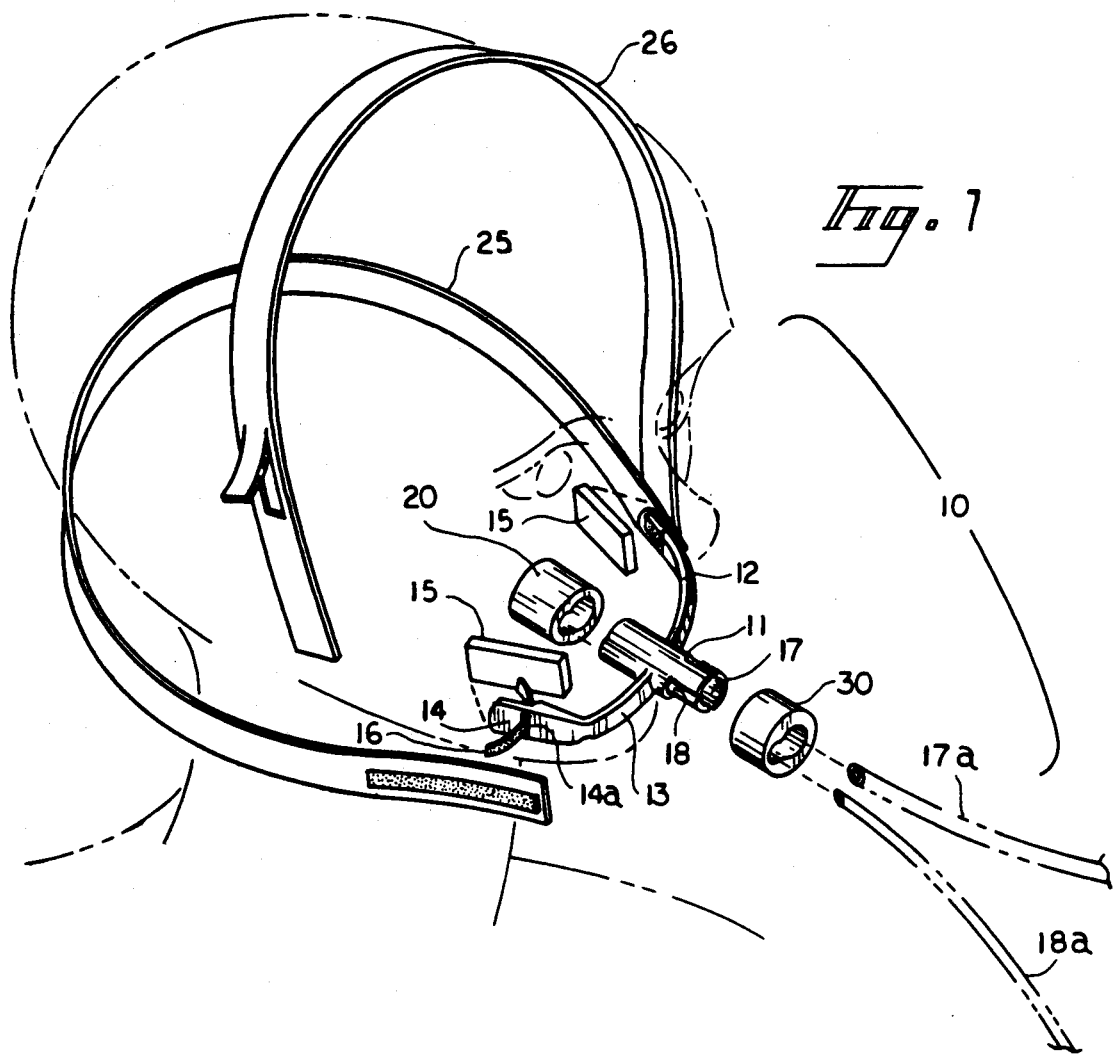
FIG. 1 shows an exploded view in perspective of the endotracheal tube holder.

The present endotracheal tube holder 10 of one piece construction is shown in an exploded view in FIG. 1. It comprises a central tubular member 11 made of clear, highly polished polycarbonate plastic for easy visual monitoring of the endotraceal tube positioning and two curved pliant wings 12,12 :, extending on either side of the tubular member 11. The wings 12,12 have long narrow sections 13,13 that allow for access to the mouth of the patient in the event that a feeding tube is in the smaller offset passageway 18 and end portions 14,14 that are widened as shown in FIGS. 3 and 4. The long narrow ssections13,13 are highly polished to allow for visual monitoring of the patient's lips. Sores often develop on the lips and the corners of thhe mouth. This willl allow for the earliest treatment of these conditions. The end portions 14,14 are widened to provide for greater surface contact between the tube holder 10 and the patient. The ends 14,14 rest against the hard surface of the jaw rather than the soft tissue of the cheeks. Adhesively attached on both sides to these widened end portions 14,14 are VELCRO fastener strips 16,16 for attaching a headband 25 to the holder 10. The strips 16,16 are slipped through slots 14a,14a, with one end of the strips 16,16 bonded on either side of the widened end portion 14,14. The headbands 25 and 26 attaching to the outside have reciprocal fasteners 16a,16a. This VELCRO headband arrangement allows for easy and quick adjustment of the holder 10 with the headband 25,26 around the head of a wearer. Cushioning cheek padding 15,15 is attached to the inner side of end portions 14,14 by affixing it to the strips 16, 16. They are easy to remove and replace when they become soiled with blood and saliva allowing medical personnel to keep their charges clean and comfortable.

Figure 2:
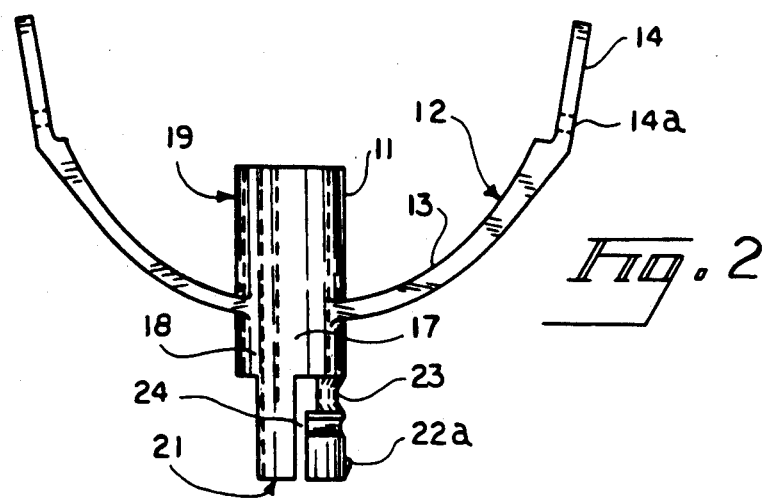
FIG. 2 shows a side view of the endotracheal tube holder.

The central tubular member 11 consists of an elongated member having two separate passageways 17 and 18 best shown in FIGS. 2 and 3. Passageway 17 is the large central passageway that holds an endotracheal tube 17a. The smaller passagewaY 18, offset to the side, is for holding a feeding tube used for infants or a nasogastric tube used for adults 18a. This passageway 18 may alternatively be used as a guide to suction deep oral secretions which pool in the rear of a patient's mouth. The main portion of the tubular member 11 and the rest of the holding device 10 is made of a clear polycarbonate that is pliant and flexible. The outer portion 19 of the tubular member 11 that extends into the wearer's mouth is hardened using appropriate polymer hardening technologies. This section 19 serves as a bite block. Some patients wearing this device with endotracheal tubes may be convulsive, biting down on the section 19 of the tubular member 11. The hardening of this section helps to prevent them from cutting off the tubes 17a,18a. A sleeve 20 of soft rubber material can be slipped over hard section 19 so as to offer comfort. This would help protect the naked gums of newborn infants or other patients suffering from tooth loss from the uncomfortable wear and abrasion of biting on a hard surface. It would act like a nipple to give a sucking reflex in an infant, thus helping to calm the infant. The soft sleeve also serves to prevent the condition known as cleft palate by spreading out the contact surface of the tube holder in the patient's mouth. The devices 10 used for infants, usually premature-birth "preemies", would be scaled down in size accordingly.

Around the opposite end 21 of the tubular member 11 is an attachment means 22 for a collet 30 used to compress the tubular member 11 in holding an endotracheal tube stationary in relation to the holder 10 and the wearer. The attachment means comprises cantilever snaps 22, 22 and an interference groove 23, seen in FIGS. 4 and 5, on the tubular member 11. The snaps 22, 22 prevent the collet 30 from sliding off the tubular member 11. Interference groove 233 mates with the annular ring 31, shown in FIG. 6, on the collet to compress the tubular member 11 onto the endotracheal tube. The annular ring 31 is size specific in that it fits only a certain sized endotracheal tube. The interference groove 23 is a continuous groove completely encircling the full diameter of the tubular member 11. The collet 30 would have a shaped hollow space 332 to allow it to mate with the tubular member 11 in a close fit. Again as before the collet 30 is constructed of a highly polished, clear polycarbonate plastic. Cantilever snaps 22, 22 are blocked by shoulders 33, 33 thus keeping the annular collet 30 affixed to the tubular member after it is initially engaged. The collet 30 compresses the tubular member 11 together in the region of slot 24. The collet 30 can be loosened by disengaging the annular ring 31 from the interference groove 23. Again, as before, the collet 30 is constructed of a clear polycarbonate.

It is to be understood that the present invention is not limited to the sole embodiment described above, but encompasses any and all embodiments within the scope of the following claims.

I claim:

1. A medical tube holder including:
   a tubular member having two separate parallel passageways, one of said passageways adapted to hold a first medical tube and the other of said passageways adapted to hold a second medical tube;
   a removable sleeve collet disposed over said tubular member;
   said sleeve collet having a partial inner annular ring member;
   flanges disposed on opposite sides of said tubular member engageable with said inner annular ring member on said sleeve collet to prevent the removal of said sleeve collet;
   said tubular member having a circumferential groove for mating with said inner annular ring member on said sleeve collet to tighten said tubular member against said first medical tube and hold it in position relative to said passageway adapted to hold said first medical tube; and
   two flexible elongated side members disposed on either side of and extending away from said tubular member and adapted to attach said medical tube holder to the face of a wearer.

2. The medical tube holder according to claim 1, wherein:

said passageway adapted to hold a first medical tube has a greater diameter than said passageway adapted to hold a second medical tube.

3. The medical tube holder according to claim 2, wherein
said passageway adapted to hold a first medical tube is disposed substantially toward a center axis of said tubular member; and
said passageway adapted to hold a second medical tube is disposed offset from said center axis of said tubular member.

4. The medical tube holder according to claim 1, wherein:
said flexible elongated side members have a long thin portion disposed adjacent said tubular member and a shorter widened flat portion disposed at the ends distal said tubular member.

5. The medical tube holder according to claim 4, wherein:
said shorter widened flat portion has affixed on an inner side, facing said tubular member, cushioning means for resting against a wearer's face, and on an opposite external side of said shorter widened flat portion is affixed attachment means for attaching the free end of a headband;
a headband is attached at both of said shorter widened flat portions on said opposite external sides, said headband for placement around the head of the wearer for securing the medical tube holder in place.

6. The medical tube holder according to claim 1 wherein:
said passageway adapted to hold a first medical tube is substantially longer than said passageway adapted to hold a second medical tube.

7. The medical tube holder according to claim 1 wherein:
said tubular member is adapted for placement in a wearer's mouth, said tubular member having a soft pliant non-abrasive covering that will not irritate the mouth of a wearer.

8. The medical tube holder according to claim 7, wherein:
said soft pliant non-abrasive covering comprises a removable sleeve.

9. The medical tube holder according to claim 2, wherein:
said first medical tube is an endotracheal tube;
said second medical tube is a feeding tube.

* * * * *